US006209545B1

(12) United States Patent
Zhukova et al.

(10) Patent No.: US 6,209,545 B1
(45) Date of Patent: Apr. 3, 2001

(54) METHOD FOR RECOVERING PERIPHERAL NERVES FUNCTIONALITY

(76) Inventors: Elena Jurievna Zhukova; Olga Valentinovna Zhukova; Svetlana Jurievna Zhukova, all of ul. Junych Lenintsev, d. 79, korp. 6, kv. 49, Moscow, 109443 (RU)

( * ) Notice: Subject to any disclaimer, the term of this patent is extended or adjusted under 35 U.S.C. 154(b) by 0 days.

(21) Appl. No.: 09/269,380

(22) PCT Filed: Jul. 9, 1997

(86) PCT No.: PCT/RU97/00215

§ 371 Date: Mar. 22, 1999

§ 102(e) Date: Mar. 22, 1999

(87) PCT Pub. No.: WO98/14158

PCT Pub. Date: Apr. 9, 1998

(30) Foreign Application Priority Data

Sep. 30, 1996 (RU) ........................................ 96119662

(51) Int. Cl.[7] ........................................ A61B 17/04

(52) U.S. Cl. ........................................ 128/898

(58) Field of Search ........................ 128/898; 601/134, 601/135

(56) References Cited

U.S. PATENT DOCUMENTS 5,501,657 * 3/1996 Feero ........................................ 601/40

* cited by examiner

*Primary Examiner*—David J. Isabella
(74) *Attorney, Agent, or Firm*—Notaro & Michalos P.C.

(57) ABSTRACT

The method for recovering the peripheral nerve function includes a manual massage along with the nerve. In so doing, the palpation of a peripheral nerve is performed to determine its nerve condition, followed by applying a pressure deep into the soft tissues with a finger at least once and then moving the finger along the peripheral nerve towards the periphery.

10 Claims, No Drawings

METHOD FOR RECOVERING PERIPHERAL NERVES FUNCTIONALITY

FIELD OF THE INVENTION

The present invention relates to the medicine, and more precisely, concerns the method for recovering the peripheral nerve function.

BACKGROUND OF THE INVENTION

It is known that the nervous system is the most integrated system of the human body, representing both structurally and functionally a single whole. In this connection, even its local injuries impact the functionality not only of neighboring structures but also of those ones located remotely. The nervous system lesion is accompanied by a variety of disturbances of internal organ functions caused by disruption of normal regulating functions of the nervous system in the case of its pathology. All kinds of the nervous system diseases are accompanied in one degree or another by the vegetative disturbances. The autonomic nervous system pathology and its dysfunctions influence the origin and course of some somatic diseases. Vegetative disturbances lead to disorders of internal organs, endocrine system, blood vessels, thermoregulation and metabolism. Different viscero-functional, neuro-vegetative, nervous and subjective disorders due to their variety can simulate many organic diseases so that a great variety of diagnoses and strangest diagnoses can be applied to them, especially if the clinical examination did not define the essential objective changes in the human body. Even a mental and physical fatigue may produce all subjective pathologic symptoms and thus simulate the whole clinical pathology. All this can cause the real functional disorders which do not only simulate a disease, but even produce it, reaching the originating of visceral diseases (dysfunctional disorders at the beginning, and then organo-dystrophic ones); in psychiatric practice such cases include the spectrum from simple behavior disturbances to serious mental pathological disorders and to the psychopathology. It happens because the fatigue impacts the nervous system, organs and tissues by toxic, dismetabolic and chemical reflections which can give rise to many serious diseases, for example, to activate the latent tuberculosis, to cause an outbreak of the infection disease, or allergic manifestation, or even the cancer (see the book A. Peunesku-Podyanu. "Difficult cases. Indefinitely expressed and difficult explained sufferings", Medical Publishing House, Bucharest, 1976, pp. 215–216). The medicamental treatment of peripheral nervous lesions, and also the therapeutic physical training in combination with the general massage are well known at present Small Medical Encyclopedia. Moscow, Great Russian Encyclopedia Publishing House, 1991, vol. 3, pp. 551–552). However, such treatment does not always ensure the full recovery of functions of traumatized peripheral nerves.

It is known that a neurologist has no possibility to see the pathology focus and, with rare exceptions, cannot palpate or auscultate it because the central nervous system is locked in the bone shells (skull and vertebral column), and peripheral nerves are mainly disposed in the depth of soft tissues A. M. Pulatov et al. "Propedeutics of nervous diseases", published by "Irfon", Dushanbe, 1970, p. 5).

It is well known from the general physiology of excitable membranes B. M. Khodorov, "The Handbook of Physiology", vol. "General physiology of excitable membranes", Leningrad, Nauka Publishing House, 1980), that stretching the peripheral nerves increases the number of "rapid" sodium ion channels in the activated state, and decreasing of their stretching leads correspondingly to decreasing the number of activated sodium channels. Increasing the number of "rapid" sodium channels in the activated state leads, as it is well-known, to increasing the generation frequency of operation transmembrane potentials and to raising the tonic bioelectrical activity of corresponding nerves. On the contrary, decreasing the number of activated "rapid" channels leads correspondingly to decreasing tonic bioelectrical activity of peripheral nerves.

The method for recovering the peripheral nerve function by means of performing the massage along a nerve is well known (SU, 1569013, Al, Int.Cl$^5$. A 61 H 25/00, 1990). When treating by this method, the vibrating massage is acted along with the damaged nerve and reflexogenic zone corresponding to it with a vibrating massage apparatus in sequence at predetermined increasing frequencies and during the predetermined time in each seance. This method allows only to improve the patient condition but cannot completely restore functions of the peripheral nerves innervating different organs and systems of the human body, because the apparatus massage (including vibromassage, hydromassage, vacuum massage) does not ensure to differentiate the treatment finely. Thus this method does not allow to mobilize the trophic function of peripheral nerves, to improve metabolism processes in ischemic nervous trunks, does not decrease the hypertension of peripheral nerves. This method does not also allow to normalize the metabolism of different organs and to treat diseases caused by lesions of corresponding peripheral nerves.

DISCLOSURE OF THE INVENTION

The basis of the present invention is the task of providing a method for recovering the peripheral nerve functions in which method, through mobilizing the trophic function of peripheral nerves, improving the metabolism processes of ischemic nerve trunks, and decreasing the high tension of peripheral nerves, the achievement is reached for more complete recovering functions of peripheral nerves innervating different organs and systems of the human body, which permits to normalize the metabolism of various organs and to treat the diseases caused by lesions of corresponding peripheral nerves.

This task is solved by that in the method for recovering the peripheral nerve functions, in which method a massage is performed along with the nerve, in accordance with the present invention, the massage is performed by hand therewith palpating at least one peripheral nerve to determine its condition, and then at least once pressing deep into the soft tissues with a finger, and moving the finger along the peripheral nerve to the periphery.

It is expedient the finger to be moved along the peripheral nerve by intermittent oscillatory motions.

It is also expedient an additional palpation to be made before moving the finger along the peripheral nerve.

It is desirable, if a compacted intumescence is detected in the peripheral nerve in the course of its palpation, to knead and smooth said compacted intumescence after said palpation.

It is also desirable the peripheral nerve, after palpating it by a finger of one hand, to be fixed in the given section, the pressure deep into soft tissues and movement along the peripheral nerve to the periphery being performed with a finger of the other hand.

It is possible, after palpating the peripheral nerve, to strike easily on the spine processes of the vertebrae and in paravertebral areas.

It is also possible, after palpating the peripheral nerve, to shift the sacrum-coccygeal junction until releasing the nerve compression in this area.

It is expedient, after palpating at least two peripheral nerves, to inspect the states of vitally important organs, then to press deep into soft tissues by a finger and to move the finger first along the peripheral nerve recovering the innervation of a vitally important organ.

This method for recovering the peripheral nerve functions allows to make an early diagnosis of the pathology being formed, and to treat a disease at the stage of its beginning. This invention allows to improve the blood circulation and metabolism in organs of the human body and in the course of a complex treatment using medicaments, since their most effective influence is reached. This invention also allows, reducing the increased tension of peripheral nerves, to achieve the more complete recovery of functions of peripheral nerves innervating different organs and systems of the human body, which allows, in tum, to normalize the metabolism of different organs and to treat the diseases caused by lesions of corresponding peripheral nerves.

Diseases have different etiology and pathogenesis, and very different clinical picture, the development mechanism of most part of them is related to the disturbances of the peripheral nerve function and, in neglected cases, also to the disturbances in the peripheral nerve structure, including the dysfunctional of the vegetative nervous system. The treatment and prophylaxis of diseases connected with the recovery of disturbed peripheral nerve function by means of this method allows to rehabilitate, with high efficiency, in a rapid mode, without employing an expensive and not readily available equipment, the patients and invalids considered slightly responsive or unresponsive at all to the effective treatment by usually methods to the present day, and, beside the stable remission, in most cases allows to initiate the regress of the diseases. The invention also allows to recover disturbed peripheral nerve function by means of generalized unblocking the spinal column, achieving the maximum possible movability of the spine in all its segments by removing primary and secondary functional blocks and recovering maximum possible disturbances of body functions, and thus to achieve the curing effect in different nosologic forms, in particularly, to increase movability of joints, to decompress the spinal canal, to eliminate the pain syndrome in diseases of the locomotor and nervous system, in various neuritis, neuralgia, arthritis, ossalgia, arthralgia, to achieve the restoration of the normal function of the heart and blood vessels in the vegeto-vascular distonia, to normalize the arterial pressure and the frequency of heart beats in the hypertensia and vaso-renal hypertensia, to eliminate the myocardium ischemia and ischemia of other organs in the cases of spastic conditions of different vessels (e.g. obliterating endarteritis, Raynaud's disease, Princmetall's stenocardia) and others. In contrast with the apparatus massages (including vibromassage, hydromassage, vacuum massage and pneumo-massage) this invention ensures to differentiate precisely the methodology of the massage. As distinct from this method, the manual therapy can also have negative effects without knowledge of nervous regulatory impacts. In comparison with the proposed method, the acupressure is less effective. The given method ensures a good succession of medical, rehabilitative, and sanitary-prophylactic measures for a considerable part of population. The method takes shorter time for curing and provides maximum efficiency. It is safe in the view of allergic complications and does not require expensive facilities. A systematic approach is maintained in the treatment on the basis of this method. It can be applied to a patient of any age ranging from a newborn baby to a person of an old age. This method is also of a certain value in the rehabilitation of patients with the residual encephalopathy (child cerebral palsy). Using it for such patients helps to eliminate muscular contractures, improving trophic processes in disturbed extremities and causing the development of considerable positive changes in recovering the lesion extremity movements, thus leading to the improvement of muscular flexibility and elasticity.

The essence of the invention will be further illustrated below by specific examples of its embodiments.

PREFERRED EMBODIMENT OF THE INVENTION

The method for recovering the peripheral nerve functions consists in performing a manual massage along with a nerve. In so doing, a palpation of at least one peripheral nerve is conducted to determine its condition. Then, at least once, a pressure is applied with a finger deep into soft tissues till sensing the nerve, and the finger is moved along the peripheral nerve towards the periphery. In this case, the finger can be moved by intermittent oscillatory motions. The condition of the peripheral nerve, in particular its tension, is determined by the palpation. Before moving the finger along the peripheral nerve, its additional palpation can be conducted. If a compacted intumescence is detected in the nerve during its palpation, the kneading and smoothing of the compacted intumescence is performed. Sometimes problems occur connected with decreasing the nerve tension. In this case the nerve is fixed at the determined section with a finger of one hand after the palpation, while a finger of the other hand presses deep into the soft tissues and moves along the peripheral nerve to the periphery. In the case of pinching a nerve excessively tensed by calcifications, after palpating and before decreasing the nerve tension, the nerve pinching is removed by destructurizing said calcifications with easy strikes, for example, with a palm edge on the spine processes of the vertebrae and in paravertebral areas. In the case of pinching the sacrum plexus nerve, after palpating and before performing procedures to decrease the tension of said nerve, the sacrum-coccygeal junction is shifted till releasing the nerve compression in this area. In the case of diagnosing the increased tension of at least two peripheral nerves, the inspection of states of vitally important organs is carried out after palpation. Then the tension of peripheral nerve innervating vitally important organs is first decreased, and then the tension of the other peripheral nerve or nerves are decreased by means of pressing deep into the soft tissues with a finger and moving the finger first along the peripheral nerve restoring the innervation of the vitally important organ.

The presented method for recovering the peripheral nerve functions is carried out as follows.

The patient examined with classical methods is laid prone on the massage table and the palpation is carried out enveloping his (or her) spinal column with two fingers of one hand and gaining the pressure on fingers of the first hand with fingers of the other hand. After receiving information on the state of the spinal column and its calcification the condition of peripheral nervous fibers is examined by the palpation to determine their tension. The increased tension of the peripheral nerve or a number of such nerves after a trauma, stress, fatigue, born infectious disease, supercooling etc. changes the nerve structural and functional organization and creates the pathology of the organ innervated by such nerve (nerves), thus leading to a number of diseases which cannot be treated with known medicamental and non-medicamental methods. The palpation of the nerve tension is performed with finger-cushions indirectly (through the muscles in the case of deep location) or directly (in the case of superficial location) placing fingers perpendicularly to the palpated surface in the area of the nerve location. The palpation of a nerve is carried out with fingers in the same way as in the case when other organs are palpated and completely in accordance with well-known methods (see the book Small Medical Encyclopedia. Moscow, Great Russian Encyclopedia Publishing House, 1991, vol. 4, pp. 226–227). Making oscilatory motions from side to side and deepening fingers into the soft tissues, the nervous bar is detected and the degree of its tension is determined on the basis of its condition. The criteria of nerve tension are: nervous characteristics (thickness, solidity, displaceability, intumescence); presence of the patient painful sensation during palpation; irradiation of the pain to other areas. The nerve tension decrease is carried out by applying a transverse force to it, i.e. by pressing a finger placed perpendicularly to the nerve axis deep into tissues. In so doing, the intermittent motions should be made along the nerve towards the peripheral. The oscillatory motions are performed permanently with a finger without taking it off the nerve (to keep the nerve in the field of sensation), and at the same time the finger moves along with the nerve, applying a transversal pressure to the nerve, i.e. rendering the pressure perpendicularly to the nerve axis. Such manipulation is repeated till the nerve tension decrease. The determination of the nerve tension or effectiveness of its decrease is performed by frequent oscillatory motions of small amplitude from side to side and on the basis of characteristics of a palpating nerve slipping under the fingers (thickness, solidity, displaceability and intumescences); and a judgment about the nerve tension can also be made on the basis of patient pain sensations. A gradual nerve tension decrease manifests itself in increasing the palpated bar displaceability and decreasing its solidity till it becomes faintly palpable and till the absence of patient pain sensations, which are criteria of the normal nerve tension. The exceptions are peripheral myelopathies (and system demyelining diseases) when the disturbance of the myelin resynthesis by Schwann cells and their destruction take place, and then the dystrophia of axial cylinders and their fragmentation occurs; when this process reaches the certain stage, the nerve trunks defined earlier by palpating as being in the pathological tension condition, cease to be felt. An indirect (through muscular layers) or direct (with more superficial location) pressure onto the nervous trunk being a part of large vascular-nervous bundles stimulates a better functioning of nerve vessels of those trunks. Thus, the improving of a microcirculation in the nerve itself excites an intensification of its own trophism, normalization of the myelin synthesis, and optimization of the neurolemmocytes (Schwann cells) renewal, which entails a normalization of disturbances of the nervous conductivity in an area subjected to the pressure, improvement in supplying the tissues surrounding the nervous trunk and innervated by its branches through normalizing the functioning of vegetative fibers (the trophic function of the vegetative nervous system) being a part of a given nerve, and facilitation of the nervous-muscular conductivity. All this allows to utilize this method in the complex treating of various diseases of different organs and systems (nervous, cardiovascular, and other). A reflex mechanism is not excluded. A removal of the muscular block is also used in diseases of the spine, spinal cord and roots. This method permits to act with the maximum precise direction onto nervous trunk on the basis of their topography in order to give rise to the previously described useful result. The pressure performed by finger-cushions is sufficiently soft and does not hurt. All organism components are in such interrelations between them, which may be characterized as the dynamic equilibrium. A maintenance of this equilibrium is the basis for keeping the relative constancy of the organism homeostasis. The nervous system plays one of the main roles in this maintenance, which system makes the human organism to be structurally and functionally a single whole. An existing basic (physiologic) tension of peripheral nerves of one areas is balanced with such tension in other areas. A local increase of individual nerves in pathology entails negative changes not only in neighbor areas, but also in remote regions.

A danger for developing the acute cardiac insufficiency, and even a possibility of the lethal outcome in restoring operations on kidney arteries of patients with a combination lesion of the kidney and coronary arteries is an example of the non-observance of the dynamic equilibrium maintenance principle. Even a successfully performed operation permitting to restore the kidney blood flow does not ensure a total convalescence of the patient due to a remained unremoved reason of the ischemization of another vitally important organ, the heart Yu.I.Buziashvili. <<Ischemic disease in combination with the renovascular hypertension".—Moscow: publication of the Bakulev Institute of Cardiovascular Surgery (ICVS), 1994, pp. 4–7).

Lesion of the nervous system provokes a disturbance in a functioning of internal organs, which is connected to a disintegration of nervous regulatory impacts. Using the proposed method, it is possible to reach an improvement in a functioning of some internal organs (mobilizing the trophic function of the parasympathetic nervous system, improving the metabolism in the ischemic nervous trunks themselves, releasing muscular blocks, reflex action), but at the same time it is necessary to monitor a condition of other organs because change of the tension of these nerves (even returning it to its base state) can render a negative influence in certain sections. Thus, improving an internal organ functional activity with the proposed method, it is always necessary to monitor a work of the heart, lungs and other vitally important organs (since the disturbance of at least one of their functions could cause the death of the organism), and, if necessary, efforts should be made to normalize functions of these organs, i.e. to keep the system approach. The change of systole frequency in the case of sinus tachycardia by impacting the dorsal branches of spinal nerves in five upper thoracic segments of the spinal cord can serve as an example of using the integrity of different parts of nervous system in order to reach a desirable clinical effect with the proposed method. The purposeful impact on the dorsal branches of spinal nerves in accordance with this method produces afferent pulses transmitted along the sensitive fibers of posterior roots to the posterior horns of the spinal cord. Such pulses obviously produce the inhibitory effect on the sympathetic nuclei of spinal lateral horns, which results in reducing the systole frequency. The pulses generated in impacting the sensitive fibers of the spinal nerve posterior branches located within the bounds of five upper thoracic segments of the spinal cord pass along these sensitive fibers and, through posterior roots, find themselves in the posterior horns of spinal gray substance and onto the intercalary neurons of sympathetic nuclei in the spinal cord lateral horns, and these pulses slow down the generation of signals stimulating the work of the heart in the sympathetic nuclei.

Thus, the systole frequency reduction takes place because the sympathetic influence on the heart is limited, and the influence of a vagus nerve (the parasympathetic nervous system) becomes conspicuous. The higher is the sympathetic activity level, the strongly is expressed the effect of the vagus nerve stimulation (a reciprocal influence).

Thus, in the case of diagnosing the increased tension of one or several peripheral nerves in comparison with the normal tension of other peripheral nerves, a general picture of the disease is determined and then a decision on the sequence of decreasing the peripheral nerve tension is taken. If, for example, beside other diseases, the patient suffers from the hypertension and headache, then the decrease of the tension in this case should be started from the ischiatic nerve, because after that the rush of blood to leg muscles starts at once, causing an immediate drop of the arterial pressure, and then the possibility to impact other peripheral nerves takes place. As it was mentioned above, when impacting the peripheral nerves it should be taken into consideration, that the nervous system is interrelated, and the change of the tension of some nerves can decrease or increase the tension of others. Due to this reason, the most strained nerves and their belonging to the vitally important organs should be determined first taking into consideration that the decrease of the tension of less stained nerves can lead to the increase of the tension of more strained nerves and vice versa—the decrease of the tension of more strained nerves can lead to the decrease of the tension of less strained nerves. Therefore the tension of a peripheral nerve innervating a most vitally important organ should be decreased first and then the tension of another peripheral nerve or other ones can be decreased. To decrease the tension of a peripheral nerve a transverse pressure with a finger or fingers is applied to it through the skin and subcutaneous tissues, and then, without taking away this pressure, the point of force application should be moved along the nerve toward the periphery. The change of the transverse pressure location is made by intermittent movements with an alternated increase and decrease of the movement speed. Such applying the pressure and shifting its application point are used many times during one or several sessions of treatment depending on the patient state. The length of the treatment is individual. Among procedures of applying a transverse pressure to the nerve and moving the application point along the nerve, the tension of the nerve mentioned above is periodically determined in the same way as it was described above. When decreasing the nerve tension to value corresponding to the normal tension of other peripheral nerves, the procedures mentioned above are stopped. After that a stable improvement of the patient status comes. If an intumescence of a nerve is detected when diagnosing the increased nerve tension, a process of removing the intumescence is performed before the procedures for decreasing the tension. Well-known techniques are employed for this purpose, e.g. kneading and smoothing the nerve in the place of intumescence location (see Small Medical Encyclopedia.—Moscow, Great Soviet Encyclopedia Publishing House, 1992 vol.5, pp. 176–177). The appearance of the hardened intumescence in a nerve is connected with the disturbance of the blood circulation in this nerve and with the edema of perineural spaces due to the compression of a nerve inside some anatomic canal (e.g., intervertebral foramina, intramuscular spaces, canals between bones and ligaments and so on). The hardened intumescence of a nervous trunk near the place of the strangulation is often difficult to be shifted and after cessation of applying forces the it comes back to the initial point. In order to avoid this the finger of one hand must fix the intumescence at the remotest distal point while decreasing the nerve tension with the fingers of the other hand before this point. It is well known that the calcification emerges in the spinal ligaments in the process of the normal vital activity of essentially healthy people. The spinal ligament calcification increases significantly as a result of dismetabolic changes and inflammatory processes related to a great variety of diseases, and this often leads to the compression of spinal nerves in the immediate vicinity to such ligaments. The destruction of mentioned ligament calcification in order to release nerve compression is performed by easy striking with a palm edge on the spine processes of the vertebra and in paravertebral areas. In this case, the fragmentation of the calcination occurs, and the blood circulation is improved (appearing outwardly as the skin hyperemia and increase of the local temperature), that prevents a further calcification, helps to clear the body from salt deposits, and release the nervous trunk compression. The release of muscular tension in neighboring vertebrae are also achieved by easy striking. When the patient organism is intoxicated with comminuted salts which is accompanied with some temperature rise, the described bed procedures should be stopped, and the process of talking the diuretics and rubbing the spine with the vodka should be started in this case. The sacrum-coccugeal junction undergoes changes to a certain moment,—i.e. becomes synostosis. This process is not the physiological one, and the synostosis emerges as a result of many slight traumas in this region that patients often fail to mention in collecting the anamnesis, but which are revealed by a purpose-oriented questioning. The correlation between the pain in the lumbus and the ossaglias on one hand, and the arthralgias in lower extremities of indefinite genesis with the limitation of active and passive movements in leg joints and the immobility of junctions, on the other hand, was revealed. The sacrum-coccygeal junction synostosis is the reason of the compression of nerves passing through this region and their pathological tension, and of nerves coming out of the spinal cord segments located higher. Basing on the clinical experience, it can be said that synostosis does not always reach its final stage, and the moveability of the coccygeal bone in the sacrum-coccygeal junction can be restored. This is released using fingers “per rectum”, the coccyx being shifted from behind warily. The significant improving in the coccygeal moveability is achieved gradually (sometimes during several sessions) without rough manipulations. The criteria of a correctly made manipulation are: a decrease of painful sensations in the coccygeal area (which emerge in the course of procedures) or their absence at all, a disappearance or decrease of the pain in the lumbus, joints and leg bones, an increase of the volume of active and passive movements in the lumbus and the joints of lower extremities, subjective sense of the distention in the sacrum-coccygeal area. Thus, in the case when the plexus nerve is strangulated, the coccyx should be set in a position similar to that during its rectal examination P. L. Gell et al. <<Emergency orthopedia. Vertebral column>>,—Moscow, Medicina Publishing House, 1995, p. 276). The sacrum-coccygeal joint is shifted till the nerve compression in this area is eliminated.

This method was tested in clinical conditions. It was used to treat various diseases related to the disturbance of functions and also, in the neglected cases, to the dysfunction of the peripheral nerve structure including the dysfunction of the vegetative nervous system. The clinical tests of this method were conducted at the Institute of Rheumatology of the RF Academy of Medical Sciences (RAMS), (Moscow), and at the RAMS Medical Radiological Research Center (Obninsk). The examples illustrating this method for recovering the peripheral nerve function are given below.

EXAMPLE 1

The patient D., 55 years old, a school teacher. The diagnosis; Bekhterev's disease—ankylosing spondylarthritis with the lesion of peripheral joints, bilateral sacroiliitis. After the influenza the patient began feel the pain in the lumbus, and pelvic-femoral, brachial, knee and cervical joints. The muscular tonus was increased. The patient could not bend and squat, raise her left arm and straighten it in the elbow joint. The head could be turned only together with the body. The excursions movements were restrained. The deep breath was difficult and painful for the patient, causing the pains in the back and the heart area. The knee joints were swelled, the knees could not bend. The lateral surface of the hips was painful. The pains became stronger by night. It was difficult for the patient to get up in the morning. The patient was examined at the Institute of Rheumatology where the following diagnosis was made: ankylosing spondylarthritis with the lesion of peripheral joints, bilateral sacroiliitis (medical card No 13841). The following treatment was prescribed: methindol, vitamin A, physiotherapy exercises, the massage of the back. After taking methindol the pain quieted down in the period of the drug action, but later it was recommenced sharply and the patient could not move. The allergic spots of a scarlet color that appeared on the elbows began to scale off. Methindol had caused the stomach irritation. Because of sharp pains the massage and physiotherapy exercises were impossible. The disease was progressing. The patient had appealed for help and agreed to be treated with the filed method. The palpation of the patient showed: the vertebral ligament calcification of soft consistency, the increased tension of spinal roots, nervous trunks and their branches pinched by spinal ligament calcification and ankylosis of apophysial joints, the increased tension of nervous trunks along the whole spinal column: n.n. cervicales ($C_I$–$C_{VII}$), n.n. thotacici ($Th_I$–$TH_{XII}$), n.n. lumbales ($L_I$–$L_V$), sacrales ($S_I$–$S_V$), n.n. coccygeus ($Co_I$–$Co_{II}$). The highest tension was observed in the plexus cervicalis resulted in the complete loss of the vertebra moveability in the cervical part; in the n. thoracalis longus that did not allow to raise an arm higher than its horizontal level; in the n.n. intercostales that led to the disturbance of thoracic respiratory excursions; in the n. femoralis that disturbed functions of the m. iliopsoas, bending the femur in the coxofemoral joint and, in the case of femoral fixation, bending the vertebral column in its lumbar section; in the n. gluteus superior, that made impossible the femoral abduction and caused a waddle gait of the patient. 20 courses of treatment by this method were given to the patient. The decrease of the tension of peripheral nerves was conducted by applying a transverse pressure to them with fingers and sing the place of pressure application along with the nerve, and by easy striking with the palm edge on the vertebral spinal processes and further moving apart the vertebrae by fingers to soften the calcification, to stop the calcification of spinal ligaments and to improve their blood circulation. Then the rubbing of the vertebral column with the vodka was carried out, and a diuretic remedy was prescribed in the form of a hips and cow-berry leaves decoction to remove calcium compounds from the body. In the first period of the treatment, the patient intoxication by comminuted calcifications, accompanied by the temperature rise up to 37.8° C. were observed during two days. For the period of the temperature rise the manual treatment was stopped but curing with the diuretic continued. On the completion of first three sessions the prescription of analgetic (methindol) was cancelled as superfluous. After that pains did not resume. As the treatment with the suggested method continued, the moveability of the vertebral column and the amplitude of extremity movements had increased drastically. To partly release the strangulation of sacrum and coccygeal nervous plexuses, the setting of patient coccyx had been made and the nerves had been straightened through the sacrum fissure. In this connection, the nature of the tension of lumbar spinal nerve posterior branches had changed radically. The decrease of their tension was conducted with the described method by easy striking on spinal processes and shifting apart the vertebrae in the lumbar area. After the tenth treatment session the condition of the patient had stabilized. After the tenth treatment session the tension of peripheral nerves had decreased to the norm, the rotation of the spinal column had been normalized, the tonus of muscles in the back had been recovered. The patient got the ability to squat easily, to bend touching the floor with her palms, to raise arms; the rotation of the vertebrae in its cervical part had been recovered, the allergic spots and heart pains had disappeared, the respiratory excursions became normal. Upon completing the treatment the pains did not resumed. During repeat examination of the patient D. the conference of specialist doctors at the RAMS Institute of Rheumatology ascertained a full recovery of her spinal column functions and an absence of peripheral arthritis. Now the patient D. leads an active life, goes in for jogging for health.

EXAMPLE 2

The patient B, 50 years old. Five years before appealing for help he started to feel unpleasant sensations like pricking, <<creeps)>> and dumbness in the I–III fingers of his right hand. He did not associate his disease with any specific reason. In the course of time pains in the arm began to appear, a bending of the hand and I, II and III fingers became difficult, the patient lost the ability to write. He took a long course of the treatment—the manual therapy, electrophoresis, radon baths, current to Bernard, massage, which did not give any result. Later the Tinnel's syndrome appeared: in easy striking on the wrist canal the pains appeared in the paresthesia of the I-III fingers. Pains became causalgic. The patient appealed for help and agreed to be treated with the filed method. The palpation of the patient showed: the increased tension of n.n. cervicales ($C_{VI}$–$Th_I$), the increased tension of the n. medianus from the brachial plexus to the branches of this nerve, and also the increased tension of the n.n. digitales palmares communes. When pressing onto the n. medianus passing under the M. flexor digitorum superficialis the tension of the n.n. digitales palmares communes and dipitales palmares proprii increases. The diagnosis had been made: the neuritis of median nerve. In line with the filed method, the treatment was started with the procedures aimed at decreasing the tension of the n. medianus to recover its finctions. In such impacting on the n. medianus passed under the M. flexor digitorum superficialis, an increas of the tension of the n.n. digitales palmares communes and n.n. digitales palmares proprii started, which caused the dumbness of the palm. In impacting on the n. medianus, its fixation was performed by pressing the point under the M. biceps brachii with a finger of one hand with decreasing the tension with a finger of the other hand along with the nerve to the place of its fixation. As a result the gradual decrease of the n. medianus tension occurred, which gave a possibility to straighten it under the M. Flexor digitorum superficialis without further increasing the tension of the n.n. digitales palmares communes and digitales palmares proprii and with the subsequent decreasing their tension according to the proposed method. In addition, an easy striking of spinal processes of the vertebrae $C_{VI}$–$Th_I$ was conducted followed by shifting them apart, kneading and smoothing the intumescences of the nn. cervicales with the subsequent multiple smoothing the n. medianus towards the periphery until a significant decrease of the tension for this nerve is achieved. After the first treatment session the patient could bend his fingers and hand, and the ability to write had restored. To consolidate the achieved effect, ten treatment sessions was given to the patient. When the normal tension of the n. medianus had been recovered the symptoms of disturbances had disappeared, the hand and finger functions had been completely restored.

EXAMPLE 3

The patient Sh., 55 years old, a teacher of music. After a long period of physical and psychological stress connected with her job where Sh. held three posts during one year, the patient came to her country cottage where she felt bad. She felt worse every hour. She complained of the headache, heaviness in the head, dizziness, diffuse pains, dumbness of extremities, nausea turning into vomiting, pains in the heart, cold fit, heart beat, difficult breathing with the impression of suffocation, tremor and faint. The patient could not get up, answered the questions with difficulties. Her body temperature was 38,5° C., arterial pressure 140/80 mm Hg, pulse rate 90 beats per minute. The ambulance was called in. The diagnosis had been made: nervous fatigue. The spasmolytic and diuretic drugs were prescribed. At the second day there was no improvement in the course of disease. The patient's relatives appealed for help. The results of medical examinations showed: all the symptoms mentioned above were still present and, besides, the swelling of face appeared. In palpating the patient the increased tension of r.r. dorsales n.n. spinales, r.r. ventrales n.n. spinales was detected. In accordance with the filed method, the patient was treated with decreasing the tension of peripheral nerves mentioned above and their branches, kneading these nerves in the places of their intumescences near the vertebral column and drawing them off towards the periphery. The patient nerves yielded to manipulations easily without significant efforts. 20 minutes after the procedure beginning the patient said that she felt quite well. 40 minutes after the procedure begining the patient's physical and psychological conditions had completely normalised. After lunch she started with enthusiasm to work in her country cottage and after their finishing went home the same day.

EXAMPLE 4

The patient Z. The diagnosis: the stable syndrome of ulnar nerve pinching; in the area of the right elbow joint. The diagnosis had been made by specialists of the Medical Radiological Research Center. The treatment was performed in accordance with the filed method for recovering the peripheral nerve functions. Five sessions of treatment were conducted. After that all functions of the ulnar nerve had been completely restored.

EXAMPLE 5

The patient B., 20 years old, was treated at the 3-d Rheumatological Department of the RAMS Institute of Rheumatology. The clinical diagnosis was: reactive arthritis (urogenous); two-sided sacroiliitis in the second stage with extra-articular manifestations. The syndrome of the joint hypermobility. The distributed secondary osteochondrosis. The conducted roentgenography of thoracic and lumbar parts of the vertebral column showed: the increased vertebral transparency; the increased concavities of supporting surfaces of lower thoracic vertebrae; slightly sharpened back angles of some vertebrae. The left-side scoliosis in the lumbar area; slightly narrowed intervertebral spaces; porosis of vertebrae. The pelvic roentgenography showed: the signs of double-sided sacroiliitis in the second stage. The structure of the heads of femurs without peculiarities. The increased radiotransparency in the area of the cotyloid cavity roofs. The narrowed fissures of some digital joints on the films of hands and distal parts of feet. Individual cyst-like enlightenments of the bone tissue. The periarticular osteoporosis of moderate degree.

At the moment of admission to the institute the following data on the patient health were registered. The patient condition is satisfactory; the constitution is regular; the nutrition is adequate; the behavior is active; the consciousness is lucid. The common integuments are clean and of usual color; the cyanosis in the area of knee joints; the hands are pale and cold to the touch; hyperhidroisis. The visible mucous membranes are pink, wet, and clean. The axillary lymphonodi are slightly enlarged. The muscles are sufficiently developed, their palpation is painless. The vertebral palpation is painless; movements in the cervical and lumbar area area limited; a small painless intumescence of the periarticular tissues in the area of the right knee joint without restricting its moveability. The clinical signs of the double-sided sacroiliitis were found two weeks before the patient admission to the clinic. The treatment was conducted by the filed method for recovering the peripheral nerve finction. Seven procedures were performed. After that the patient condition was examined. The results of examination were the following.

The results of measurements of the vertebral moveability:
1. The moveability in the cervical section of the vertebral column

| a) head turnings | Right | Left |
|---|---|---|
| - at admission to the clinic | 82° | 79° |
| - before discharge from the clinic | 87° | 85° |

II. The moveability in the thoracic and lumbar sections of the vertebral column

| | | |
|---|---|---|
| a) trunk turnings with the pelvis fixed | Right | Left |
| - at admission to the clinic | 58° | 54° |
| - before discharge from the clinic | 63° | 64° |
| b) trunk bendings (the angle of the trunk bend with respect to the vertical axis) | Right | Left |
| - at admission to the clinic | 150° | 147° |
| - before discharge from the clinic | 142° | 138° |
| c) lung excursion (mm) | Right | Left |
| - at admission to the clinic | 42 mm | 42 mm |
| - before discharge from the clinic | 48 mm | 48 mm |
| d) Shober's symptom | | |
| - at admission to the clinic | no vertebrae moveability | |
| - before discharge from the clinic | vertebrae are movable | |

As a result of the treatment a positive dynamics is registered: the pains in the sacrum area and other sections of the vertebral column had disappeared, the weakness and fatigue had significantly decreased, the vertebral moveability had inreased. The patient was discharged from the institute to continue the treatment at the out-patient department.

EXAMPLE 6

The patient B, 20 years old, came to see a doctor for the first time because of heart pains, intermissions of the heart rhythm accompanied with the dyspnea. The latest annual ECG examination revealed: sinus rhythm of 75 beats per minute, a vertical position from the heart, moderate myocardial changes. During examination and on the roentgenogram the heart borders were not increased, the heart sounds were muffled, the systolic murmur was heard. It was found out from the case record that after having angina two years ago the patient had suffered from dizziness and, during physical exercises, from rapid heart beat followed by heart pains and heavy feeling behind the sternum. The patient was treated at the out patient department but nevertheless had the same complaints. Besides, new complaints about weakness and fatigue were also expressed. The patient was admitted to the RAMS Institute of Rheumatology for the examination and treatment. The examination conducted at the time of admission revealed: the heart rhythm is regular; the heart sounds are muffled; brief systolic murmurs. The ECG examination revealed diffused changes of the right part of the myocardium in contrast to the ECG examination conducted earlier without dynamics. The phonocardiographic examination (PCG) revealed: the decreased amplitude of the first heart sound; the insignificant spindle-shaped systolic murmur on the 5L and 4L. After physical exercises the systolic murmur retained its characteristics but became stronger; the prominence of the second sound on the pulmonary artery.

The echocardiographic examination revealed: internal sizes of the left ventricle and atium do not enlarged; mitral cusps are thin with regular movements; the aorta and its cusps are without any peculiarities; tricuspid cusps are thin and moveable; the right cameras of the heart do not increased. The Doppler echocardigraphic examination revealed that intracardiac blood flows have no changes. The X-ray examination of the chest revealed: the lung fields are transparent; the lung contour in the lung root adjacent zones has a slightly increased contrast, the lung roots are structural; the presence of commissures in the diaphragmatic pleura limiting the lung excursion; the heart sizes do not enlarged; the heart waist is clearly delineated; the heart position is vertical; the heart contours are clear-cut. The patient's diagnosis was: the non-rheumatic myocarditis. The rheumatic signs were not found. The disease was accompanied with the reactive Erogenous ar thritis During the patient stay in the hospital for treatment of arthritis she took voltaren, plaquenil 0.2 per day, then pananguin, riboxin, ascorbic acid. Since the patient examination revealed the tension and pinching of peripheral nerves the treatment by the method for recovering the peripheral nerve functions was started along with the symptomatic treatment specified above. The institute specialist conducted seven procedures in the course of the patient treatment, with the result that her condition improved considerably and she was discharged from the institute in a satisfactory status of health. The pains in the heart area had disappeared, the weakness, fatigue, dyspnea in the process of a physical work had become much less, the lung excursion increased, the sonority of heart sounds could be heard during the auscultation, murmurs had disappeared, the cryoglobulinemia and the antinuclear factor of the blood had also disappeared.

The treatment with this method was continued after the cancellation of the all other procedures, and ten procedures were conducted additionally. The patient appealed to the Surgical Research Center of RAMS for consultations to confirm the diagnosis of the myocarditis and to obtain the recommendations on her further treatment. The examination conducted in the course of these consultations revealed no signs of the myocarditis. The ECG examination showed: the heart rhythm is sinus, the heart axis position is vertical; the ECG picture has no peculiarities. The phonocardiographic examination showed: the amplitude of heart sounds is normal; pathologic sounds are absent; murmurs do not registered. The conclusion of the Surgical Research Center was: there are no data on pathological changes in the heart.

EXAMPLE 7

The patient B, 51 years old. After a craniocerebral injury the patient was treated at the neurosurgical department of the City Clinical Hospital No. 7 in connection with a light bruise of the brain. The vasodilative hypotensive, nootropic, symptomatic therapy was conducted, as a result of which the neurologic symptoms decreased significantly.

However, the examination performed by the neuropathologist of the Botkin Clinical Hospital revealed: some decrease of the pupillary reaction to the light, manifestations of the osteochondrosis in the cervical part of the vertebral column, of the deforming spondylosis and, as a result, the tortuosity of the vertebral artery and the distinct decrease of the blood flow in it confirmed by the results of the dopplerographic examination of brachial and cephalic arteries.

The linear velocity of the blood flow in common carotid arteries was 78 cm/s from the left, 74 cm/s from the right. A linear velocity of the blood flow in the internal carotid arteries was 60 cm/s from the left, up to 45 cm/s from the right. An S-shaped tortuosity of the right carotid artery.

The path of both vertebral arteries passing between the transverse processes of cervical vertebrae was shifted. There was an S-shaped tortuosity of the extravertebral section of both vertebral arteries. A linear velocity of the blood flow in the vertebral arteries was 57 cm/s from the left, 34 cm/s from the right.

During all the period of treatment as to the craniocerebral injury, despite the conducted therapy, the patient permanently had the stable increased arterial pressure. The arterial pressure of 170/30 mm Hg was registered in the course of the examination conducted by the neuropathologist of the Botdkin Hospital.

As it was assumed that a stable increased arterial pressure had a compensatory-reflex basis due to distinct cerebral hypoxia, the treatment using the proposed method was undertaken.

Ten sessions of the treatment aimed at the peripheral nerve function recovery were conducted not only in the spinal cord cervical part but also in the lumbosacrum area.

The result of the treatment was the considerable improvement in the patient general condition, manifested particularly in the better vertebral moveability and rotation, in the essential decrease of the arterial pressure, and in the improvement of the cerebral arterial blood flow.

The repeated examination revealed: the arterial pressure is 130/95, a linear velocity of the blood flow in common carotid arteries is 92 cm/s from the left, 94 cm/s from the right.

The filed method ensures the full recovery or essential improvement of conditions for the patients suffering from diseases connected with peripheral nerve function disturbances, including the cases of some diseases considered to be incurable.

Thus, the results of clinical trials of this invention allow to conclude that this method for recovering the peripheral nerve fimction, based on the mobilization of the trophic function of peripheral nerves, on the improvement of the metabolism in the ischemic nervous trunks, on the relaxation of the increased tension of peripheral nerves, ensures better recovery of functions of peripheral nerves innervating different organs and systems of the human body, which in turn makes it possible to normalize the metabolism in different organs and systems of the human body and to cure diseases caused by lesions of corresponding peripheral nerves.

INDUSTRIAL APPLICABILITY

This invention can be used in the cosmetology and sport, in various branches of medicine, for example, in orthopedics, gynecology, traumatology, neurology, neurosurgery, therapeutics and surgery for treatment and prophylaxis of different diseases of locomotor system, muscular and nervous systems, cardiovascular system, endocrine and excretory systems, visual, acoustic and sexual function disturbances, psychiatric diseases etc. connected with the disturbances of the peripheral nerve function. This wide range of diseases includes the following ones: arthritis and arthrosis of different etiology, particularly, rheumatoid arthritis, arthritis combined with spondyloarthritis (seronegative spondyloarthritis), arthritis connected with the infection, intervertebral osteochondrosis and other diseases of joints, radiculitis, plexitis, neuritis and neuralgia, ossalgia, arthralgia etc; vegetovascular dystonia, atherosclerosis, hypertension, heart ischemia, Princemetal's stenocardia, Raynaud's disease, obliterating endarteritis etc. This list also includes the diseases considered before as incurable: ankylotic spondylarthritis (Bekhterev's disease), children cerebral paralysis, systemic lupus erythematosus and other diseases connected with increased tension of peripheral nerves.

What is claimed is:

1. A method of recovering function of a peripheral nerve having a periphery, the method comprising: diagnosing an increased tension of the nerve by palpating the nerve; and reducing the tension of the nerve by massaging the nerve, applying a transverse pressure to the nerve, and moving a location of application of the transverse pressure along the nerve, toward the periphery of the nerve.

2. A method according to claim 1, wherein the step of moving the location is performed by intermittent motions with alternate increase and decrease of the speed of said moving.

3. A method according to claim 2, wherein the steps of applying the transverse pressure to said nerve and moving said transverse pressure application location along said nerve toward its periphery are performed repeatedly.

4. A method according to claim 3, wherein the tension of said nerve is diagnosed periodically between said steps of applying the transverse pressure to said nerve and moving said transverse pressure application location along said nerve.

5. A method according to claim 4, including detecting a hardened intumescence of the nerve, eliminating said intumescence by kneading and smoothing said nerve in the location of the intumescence before the steps of applying the transverse pressure and moving the transverse pressure application.

6. A method according to claim 1, including massaging the nerve manually.

7. A method according to claim 1, including drawing off the nerve by clasping it with fingers of one hand of a person performing the method and applying the transverse pressure to the nerve with a finger of the other hand of the person performing the method toward a fixation location along the nerve.

8. A method according to claim 1, wherein the nerve has a strangulation, the method including eliminating said strangulation before performing the steps of applying the transverse pressure and moving the transverse pressure location, by striking of the nerve with an edge of a palm of the person performing the method.

9. A method according to claim 8, wherein the nerve has a strangulation of its sacrum plexus, including setting a coccyx of the person having the nerve on which the method is being performed first, before performing the steps of applying the transverse pressure and moving the transverse pressure location.

10. A method according to claim 1, including reducing the tension least two peripheral nerves including the first mentioned peripheral nerve and at least one additional peripheral nerve, each having a periphery, one of the nerves being an innervation of a vitally important organ, the method comprising reducing the tension of the nerve of the vitally important organ first before performing the method to reduce the tension of the other nerve.

* * * * *